(12) United States Patent
Seshimoto et al.

(10) Patent No.: US 6,405,876 B1
(45) Date of Patent: Jun. 18, 2002

(54) BLOOD FILTER CARTRIDGE

(75) Inventors: Osamu Seshimoto; Kenichiro Yazawa; Takaki Arai, all of Saitama (JP)

(73) Assignee: Fuji Photo Film Co., Ltd., Kanagawa (JP)

( * ) Notice: Subject to any disclaimer, the term of this patent is extended or adjusted under 35 U.S.C. 154(b) by 0 days.

(21) Appl. No.: 09/464,612

(22) Filed: Dec. 15, 1999

(30) Foreign Application Priority Data

Dec. 15, 1998 (JP) ............................................. 10-355474

(51) Int. Cl.[7] .............................................. B01D 29/00
(52) U.S. Cl. ...................... 210/490; 210/488; 210/504; 210/506; 436/528; 436/531
(58) Field of Search ................................. 210/435, 446, 210/488, 489, 490, 496, 503, 504, 505, 506, 507, 508; 436/523, 528, 531, 535, 169, 170, 177, 178; 530/412, 413

(56) References Cited

U.S. PATENT DOCUMENTS

| 4,512,896 A | * | 4/1985 | Gershoni | .................... 210/635 |
| 4,623,461 A | * | 11/1986 | Hossom et al. | ............. 210/445 |
| 4,693,834 A | * | 9/1987 | Hossom | ...................... 210/767 |
| 4,975,366 A | * | 12/1990 | Sudo et al. | ...................... 435/7 |
| 4,999,163 A | * | 3/1991 | Lennon et al. | ................. 422/58 |
| 5,038,793 A | * | 8/1991 | Guirguis | ...................... 604/317 |
| 5,916,521 A | * | 6/1999 | Bunce et al. | .................. 422/56 |
| 6,045,699 A | * | 4/2000 | Yazawa et al. | ............. 210/637 |
| 6,140,474 A | * | 10/2000 | Kamada et al. | ........ 530/388.85 |

FOREIGN PATENT DOCUMENTS

EP  0785012 A1 * 7/1997

* cited by examiner

Primary Examiner—John Kim
(74) Attorney, Agent, or Firm—Reed Smith LLP

(57) ABSTRACT

The blood filter cartridge which can collect a minor component of blood efficiently in a high concentration comprises a blood filtering material and a holder containing the blood filtering material and having a blood inlet and a filtrate outlet, wherein an antibody or an antigen is immobilized on at least a part from the blood inlet to the filtrate outlet or a filtrate receiver.

1 Claim, 2 Drawing Sheets

BLOOD FILTER CARTRIDGE

BACKGROUND OF THE INVENTION

This invention relates to a blood filter cartridge for the preparation of a plasma or serum sample from whole blood.

The type or concentration of blood components, such as metabolites, proteins, lipids, electrolytes, enzymes, antigens, and antibodies, is measured, in general, using a plasma or serum sample obtained by centrifuging whole blood. However, centrifuging takes labor and time. Particularly, centrifuging is unsuitable for an urgent case of measuring a small number of samples promptly and in site inspection, because of requiring a centrifuge and electricity. Thereupon, it has been investigated to separate serum from whole blood by filtration.

Several filtration methods using glass fiber filter have been developed wherein whole blood is charged into the glass fiber put in a column from one side of the column, and pressurized or evacuated to obtain plasma or serum from the other side (Japanese Patent KOKOKU Nos. 44-14673, 5-52463, Japanese Patent KOKAI Nos. 2-208565, 4-208856).

However, practical filtration methods capable of obtaining an amount of plasma or serum from whole blood necessary for measuring by an automatic analyzer have not been developed except a part of items, such as blood sugar.

On the other hand, the inventors developed a blood filter cartridge composed of a filter holder and a syringe. The filter holder is composed of a holder body which contains filter material and a cap which is screwed on the holder body. The filter material consists of, e.g. two sheets of glass fiber filter, one sheet of cellulose filter and one sheet of polysulfone microporous membrane (FIG. 1 of EP 785430 A1)

Another blood filter cartridge composed of a holder body and a cap was also developed. The holder body consists of a plasma receiver located on the upper side and a filter chamber located on the underside. The filter material put in the filter chamber is composed of six sheets of glass fiber filter and one sheet of polysulfone microporous membrane (Example 1 of EP 785012A1).

The inventors further developed various blood filter cartridges, and their patent applications were made (Japanese Patent KOKAI 10-227788, 10-185909, 10-185780, etc.)

Incidentally, there are various blood components, and contents of some of them are very small. Heretofore, the analysis of the minor components were made possible by the improvement in the analytical sensitivity. However, the analysis requires a large scale analyzer and expensive cost, and nevertheless, the analytical accuracy tends to be not enough.

SUMMARY OF THE INVENTION

An object of the invention is to provide a means capable of measuring minor components contained in blood simply, efficiently, and with a high analytical accuracy.

After investigating eagerly so as to develop the above means, the inventors noted the blood filter device which is used for the preparation of plasma or serum samples for the analysis of blood components. That is, the volume of blood being filtered is considerably more than the volume of plasma or serum samples subjected to use. For example, a blood component can be analyzed using only a volume of 10 $\mu$l or less by a dry analytical element, i.e. several analytical items can be analyzed using several tens $\mu$l. Nevertheless, the volume of blood being filtered is from several hundreds to thousand $\mu$l. Thereupon, when an antibody to an antigen to be measured or an antigen to an antibody to be measured is immobilized on a blood filter device, the minor component which is the antigen or the antibody can be concentrated. By subjecting the immobilized matter to analysis, the minor component can be analyzed with a high accuracy.

The present invention has been achieved based on the above conception, and provides a blood filter cartridge which comprises a blood filtering material and a holder containing the blood filtering material and having a blood inlet and a filtrate outlet, wherein an antibody or an antigen is immobilized on at least a part from the blood inlet to the filtrate outlet or a filtrate receiver.

Figure 1:
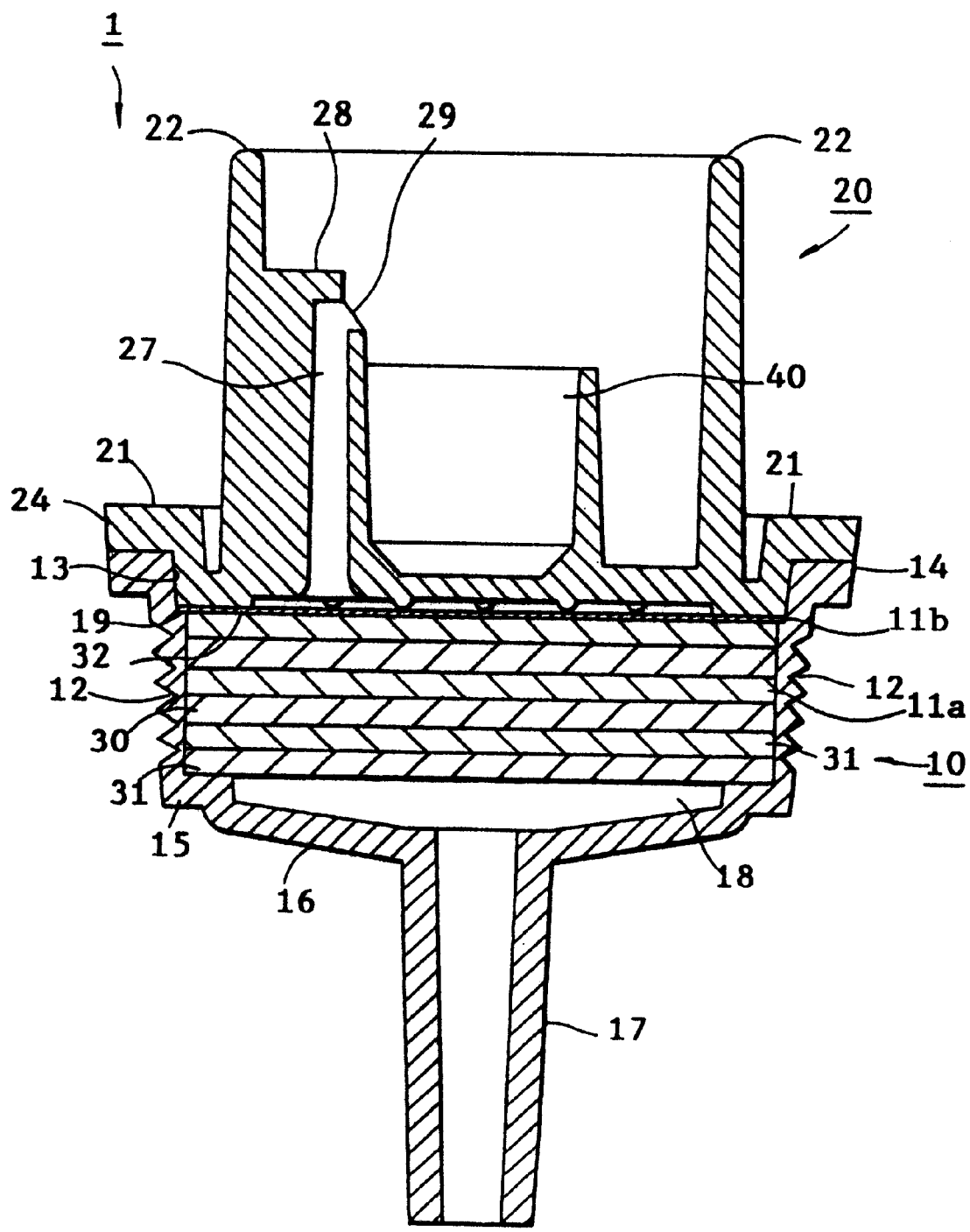
FIG. 1 is a longitudinal section of a blood filter cartridge of the invention.

1 . . . Blood filter cartridge
10 . . . Holder body
11a . . . Glass fiber filter chamber (blood filter chamber)
11b . . . Microporous membrane chamber (blood filter chamber)
12 . . . Circumpherential groove (cutting portion)
13 . . . Inclined portion
14 . . . Flange
15 . . . Fiber filter-placing portion
16 . . . Funnel-shaped disc portion
17 . . . Blood inlet
18 . . . Space
19 . . . Step portion
20 . . . Cap
21 . . . Outer wall
22 . . . Inner wall
23 . . . Opposite faces
24 . . . Flange
25 . . . Rib
26 . . . Projection
27 . . . Filtrate passage
28 . . . Pent roof
29 . . . Filtrate outlet
30 . . . Blood filtering material
31 . . . Glass fiber filter
32 . . . Polysulfone microporous membrane
40 . . . Filtrate receiver

DETAILED DESCRIPTION OF THE INVENTION

Although the type of the blood filtering material is not limited, in the filtering material of the invention, it is thought that the filter material to be used does not trap blood cells only by the surface, but catches to remove blood cells gradually by entangling at first large blood cell components and then smaller blood cell components in the space structure with permeating in the thickness direction in total of the filtering material, called the volumetric filtration or depth filtration. Preferable blood filtering material are glass fiber filter and the like, and a combination of glass fiber filter and microporous membrane is particularly preferred.

Preferable glass fiber filter has a density of about 0.02 to 0.5 g/cm$^3$, preferably about 0.03 to 0.2 g/cm$^3$, more preferably about 0.05 to 0.13 g/cm$^3$, a retainable particle size of about 0.6 to 9 $\mu$m preferably 1 to 5 $\mu$m. By treating the surface of glass fiber with hydrophilic polymer as disclosed in Japanese Patent KOKAI Nos. 2-208676, 4-208856, filtration proceeds more fast and smoothly. Lectin or other reactive reagent or modifier may be incorporated into glass fiber, or glass fiber may be treated therewith. Two or more glass fiber filters may be superimposed.

It is also possible that a glass fiber filter sheet is cut into small pieces, and packed in a holder. The thickness of glass fiber filter sheet is about 0.2 to 3 mm, usually about 0.5 to 2 mm. The glass fiber filter sheet is cut into pieces having a diameter of about 10 to 30 mm, preferably about 15 to 25 mm. The shape of the piece is not limited, and may be square, rectangle, triangle disc or the like.

Microporous membranes having blood cell-separating ability of which the surface has been made hydrophilic separate whole blood into blood cells and plasma specifically without hemolysis to the degree of substantially influencing analytical values. A suitable pore size of the microporous membrane is smaller than the retaining particle size of glass fiber filter, and is 0.2 µm or more, preferably about 0.3 to 5 µm, more preferably about 0.5 to 3 µm. The void content of the microporous membrane is preferably higher, and a suitable void content is about 40 to 95%, preferably about 50 to 95%, more preferably about 70 to 95%. Illustrative of the microporous membranes are polysulfone membrane, fluorine-containing polymer membrane, etc.

Preferable microporous membranes are polysulfone membrane, cellulose acetate membrane, and the like, and particularly preferred one is polysulfone membrane. In the blood filtering material of the invention, the glass fiber filter is located on the blood inlet side and the microporous membrane is located on the filtrate outlet side. The most preferable blood filtering material is a combination of the glass fiber filter or the aggregate of extra fine fibers and polysulfone membrane laminated in this order from the blood inlet side.

A suitable thickness of the glass fiber filter varies according to the plasma volume to be recovered and density (void content) and area of the glass fiber filter. A necessary amount of plasma for analyzing plural items using dry analytical elements is 100 to 500 µl. In practical viewpoint, a glass fiber filter having a density of about 0.02 to 0.2 g/cm$^3$ and an area of 1 to 5 cm$^2$ is suitable. In this case, a suitable thickness of the glass fiber filter layer is about 1 to 10 mm, preferably about 2 to 8 mm, more preferably about 4 to 6 mm. The above thickness can be made by superposing 2 to 10 sheets, preferably 3 to 8 sheets of glass fiber filter.

A suitable thickness of the microporous membrane is about 0.05 to 0.5 mm, preferably about 0.1 to 0.3 mm, and the number of the microporous membrane is usually one. However, two or more sheets of microporous membrane may be used, if necessary.

Respective layers may be integrated by joining each other using partially disposed (e.g. spots) adhesive, according to disclosures in Japanese Patent KOKAI Nos. 62-138756-8, 2-105043, 3-16651, etc.

The blood filtering material is placed in a holder having a blood inlet and a plasma outlet. The holder is, in general, formed of a body containing the blood filtering material and a cap, and each of them is provided with at least one aperture.

One is used as the blood inlet, and the other is used as the filtrate outlet, optionally further as a suction port. A suction port may be provided separately. In the case that the holder is rectangular and is provided with the cap on a side of the holder, both of the blood inlet and the plasma outlet may be provided on the holder body.

The volume of the filter chamber which contains the blood filtering material is necessary to be greater than the total volume of the blood filtering material both in a dry state and in a swelled state upon absorbing a sample (whole blood). When the volume of the filter chamber is smaller than the total volume of the blood filtering material, filtration does not proceed efficiently and hemolysis occurs. A suitable ratio of the volume of the filter chamber to the total volume of the blood filtering material in a dry state is, in general, 101 to 200%, preferably 110 to 150%, more preferably 120 to 140%, although the ratio varies according to the swelling degree of the filtering material. An actual volume is set depending on the necessary amount of plasma or serum, and is about 0.5 to 2.5 ml, usually about 0.6 to 2 ml, especially about 0.7 to 1.5 ml.

Besides, it is preferable that the periphery of the blood filtering material is closely fitted to the wall of the filter chamber so as not to form a bypass of whole blood without passing the filtering material.

The suction nozzle for sucking blood is connected to the blood inlet of the holder. The nozzle may be integral with or separate from the holder. In the case of a separate body, the nozzle is fixed to the holder body, and the connecting portion has a closed structure. The connecting means may be adhesion, fusion, screwing, fitting or the like.

The blood filter cartridge is made into a closed structure except the blood inlet and the plasma outlet by attaching a cap to the holder body.

As the material of the holder, thermoplastic or thermosetting plastics are preferable. Illustrative of the plastics are general-purpose polystyrene, high impact polystyrene, methacrylate resin, polyethylene, polypropylene, polyester, nylon, polycarbonate, etc. The material may be transparent or opaque.

Fitting of the cap to the holder body may be any means, such as adhesion using adhesive or fusion welding. On that occasion, either periphery of the holder body or of the cap is located on the inside, or both peripheries are butted. The fitting may be in a state of detachable utilizing screws or the like.

The shape of the blood filtering material is not restricted, but disc and polygon is preferable in view of production. By rendering the size of the blood filtering material slightly greater than the inside section of the holder body (i.e. filter chamber), breakthrough of blood at the periphery of the filtering material can be prevented. To render the shape square is preferable because of no generation of cutting loss. Moreover, cut pieces of glass fiber filter can also be served.

The blood filter cartridge of the invention may be provided with a filtrate receiver. The filtrate receiver is connected to the filtrate outlet through a wall, and the filtrate outlet is located above the liquid level of the filtrate receiver. The filtrate outlet may be provided on the upper part of the side wall of the filtrate receiver or a pipe standing on the inside of the filtrate receiver. The filtrate receiver is made into various shapes in connection with various factors, such as the relation to the position of sucking analytical sample, the relation to the blood filtering chamber, the relation to optional other parts, and the like, and, in general, cylindrical or square. The bottom of the filtrate receiver is flat, funnel-shaped, round or the like. The volume of the filtrate receiver is, in the case of preparation of analytical sample for dry analysis, about 100 to 900 µl, usually about 200 to 600 µl, and has a depth of about 3 to 12 mm and a width (diameter a side length) of about 5 to 11 mm. As to the position of the position of the filtrate outlet, the underside of the filtrate outlet is located higher than the designed liquid level of the filtrate receiver by about 0.5 to 5 mm, usually about 1 to 2 mm. Although the volume of filtrate varies according to the hematocrit value of blood, the designed liquid level is of filtering blood having a hematocrit value of 20 to 60%. The filtrate receiver may be integrated with or separated from the holder.

In the blood filter cartridge of the invention, an antibody and or an antigen is immobilized on at least a part from the blood inlet to the filtrate outlet or the filtrate receiver.

The antibody recognizes the measuring object component as an antigen. The measuring object component is not especially limited, and includes medicinal substances such as digoxin, theophylline, phenobarbital, phenytoin, penicillin and amikacin, hormones such as prostaglandin, testosterone, progesterone and thyroxin, protein hormones, such as insulin, TSH and thyoglobulin, imunoglobulins, such as IgG, IgE and IgA, viral antigens, such as HA and HB, and the like. The antibody may be either monoclonal antibody or polyclonal antibody, and monoclonal antibody is preferable because of mass producibility and uniform qualities.

If the antibody desired is commercially available, it can be used. Otherwise, the antibody may be produced according to a known method of producing an antibody. For example, in the case of polyclonal antibody, the measuring object component is injected once or several times into subcutaneous of the back, foot pad or femoral muscle of a warm-blooded animal, such as rabbit, goat, horse, guinea pig or chicken, in an amount of 0.3 to 2 mg per kg together with an adjuvant, and thereby the antibody is produced in the humoral fluid. The serum may be used as he antibody, or it may be purified according to a known purification method of antibody, i.e. immunoglobulin, from serum, such as ammonium sulfate precipitation, ion-exchange chromatography, gel filtration, affinity chromatography and the like.

On the other hand, this antibody may be produced as a monoclonal antibody. In this case, the above measuring object component is injected several times into the abdominal cavity of a mouse together with an adjuvant, and its spleen is excised. The spleen cell is fused with mouse myeloma cell by a conventional method such as by using polyethylene glycol. The hybridoma thus obtained is cultured and cloned, and the cell capable of producing the object antibody is obtained. This cell is injected into the abdominal cavity of a mouse, and multiplied. Then, ascites are collected, and the object antibody is separated from the ascites.

The antibody may be decomposed by a protease, such as persin, and used as its fragment, such as $F(ab')_2$, Fab' or Fab.

The antibody may be immobilized on anywhere from the blood inlet to the filtrate outlet of the blood filter device or the filtrate receiver, for example, a part or the whole of the blood filtering material, the inner wall of the blood inlet passage, the inner wall of the filtrate outlet passage, the inner wall of the filtrate receiver, or grains which are arranged at a suitable place. It is preferable to immobilize the antibody on a layer of blood filtering material, especially a microporous membrane, because of collecting the measuring object component in a high concentration and taking out it easily. When the antibody is immobilized on the inner wall of the blood inlet passage or the inner wall of the blood inlet passage or the inner wall of the filtrate outlet passage or the like, it is convenient on measuring the antigen bound to the antibody that the passage or the like is made separable from the blood filter device. Such a attaching means is fitting, engaging, screwing or the like.

When the antibody is immobilized on the blood filtering material, a taking out means of the blood filtering material after the finish of blood filtration is to provide a cutting portion capable of cutting the circumference of side wall of the holder. The cutting portion does not discharge filtrate during filtering blood, and is easily cuttable upon taking out the blood filtering material. The cutting means is a cutter, a knife, a saw, a metal wire, a string or were pulling by hand or a combination thereof. The shape of the cutting portion is, in principle, a circumferential groove. The section of the groove is not limited, and includes V-shaped, U-shaped, or the like. An important point is the thickness at the deepest portion of the groove. Although the suitable thickness varies according to the material of the holder and the cutting means, in general, it is about 0.05 to 1 mm, preferably 0.1 to 0.5 mm. The circumferential groove is provided at the position where the antibody-immobilized blood filtering material is present. The number of the grooves is fundamental one, but may be plural. For example, the outer periphery may be a jag formed by continuous grooves in parallel, or may be formed of a thin sheet having a thickness of the above deepest portion of the groove. In this case, the cutting portion is indicated by a print or the like. A suitable sheet is made to facillitate cutting in the circumferencial direction, such as a uniaxially oriented sheet. The periphery may be formed by stacking rings between each of which is bonded by an adhesive using a separable adhesive at the cutting portion to prevent leakage of filtrate upon blood filtration.

The immobilization can be selected from various methods developed for the immobilization of enzyme, and may be the covalent bonding, the ionic bonding or the physical adsorption. In the case of the covalent bonding, a suitable method can be selected by considering the functional groups of both substances. Such functional groups include amino groups, carboxyl groups, hydroxyl groups, thiol groups, imidazole groups, phenyl goups, and the like. As to the binding method of amino groups, many methods are know such as the diisocyanate method, the glutaraldehyde method, the difluorobenzene method, the benzoquinone method, and the like. As the method of binding amino group to carboxyl group, the peptide-binding method of carboxyl group to succinimido este, the carbodiimide method, the Woodward reagent method and the like are known. The periodate oxidation method (Nakane method) where a bridge between amino group and sugar chain forms is also utilized. In the case of utilizing thiol group, for example, a carboxyl group is first converted to a succinimido ester, and this ester group is then allowed to react with cysteine to introduce the thiol group, and both thiol groups are bound by using a thiol-reactive bifuncional cross-linking reagent such as phenylenebismaleimide. As the method of utilizing a phenyl group, the diazotization method and the alkylation method are utilized. In the case of binding to glass fiber, there is, for example, the method of reacting with an aromatic aminosilane dirivative. Other than the above, a suitable method may be selected from the various methods described in "Method in Immunology and Immunochemistry" (C. A. Williams et al., Academic Press, N.Y., 1976) and "Koso Meneki Sokutei-ho" (Enzyme Immunoasay)" (E. Ishikawa et al., Igaku-shoin (Japan), 1978).

The immobilized amount of the antibody is designed, in principle, capable of trapping the total amount of the measuring object component contained in the blood to be filtered, and the maximum content of the measuring object component in the common variation range and the designed volume of the blood to be filtered.

Two or more antibodies may be immobilized, and thereby, two or more measuring object components can be trapped. In this case, respective antibodies may be immobilized on separate blood filtering materials, such as two or more microporous membrane sheets or one microporous membrane sheet and one glass fiber filter sheet.

It is also possible to immobilize an antigen for measuring an antibody or an antigen and an antibody for measuring an antibody and an antigen simultaneously. For example, an antibody to syphilis and ASO can b measured.

After the blood filtration is finished, the inside of the blood filter device is washed optionally. The washing can be carried out by streaming pure water, a suitable buffer or the like from the filtrate outlet to the blood inlet.

The measuring object component trapped by the immobilized antibody can be measured by the sandwich method of enzyme immunoassay or the like. On the measurement, the immobilized antibody may be taken out of the blood filter device. Instead, a solution of an enzyme-labeled antibody is introduced into the blood filter device without taking out it, and the effluent is measured. The label is not limited to enzyme, and an radioactive isotope and the like can be utilized.

The blood filter device of the invention can be used for the preparation of a plasma or serum sample, and the plasma or serum sample can also be used for blood analysis.

EXAMPLES

Example 1

Figure 2:
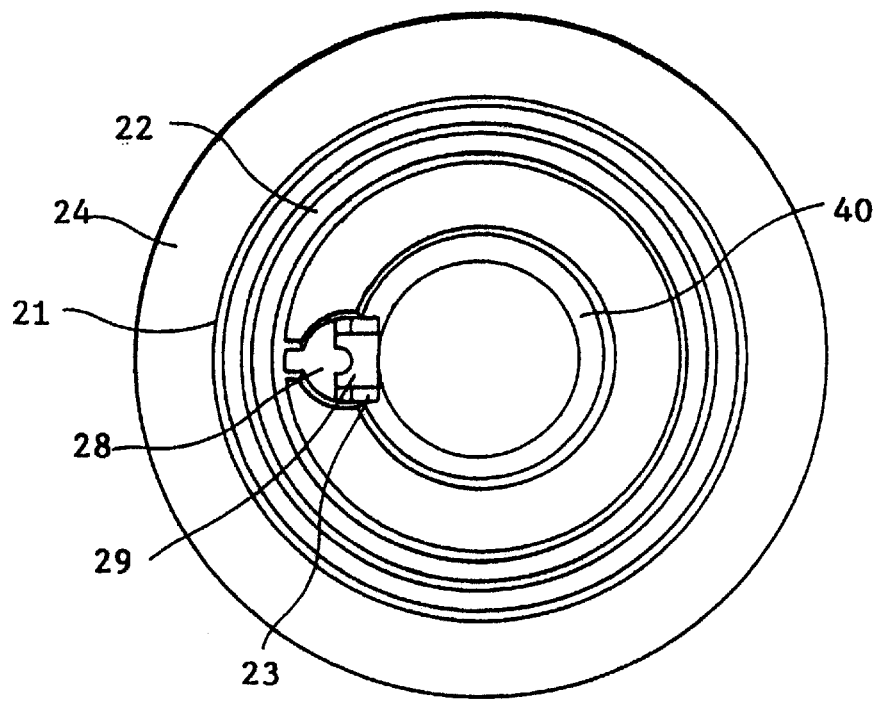
FIG. 2 is a plan view of the cap of the cartridge.
Figure 3:
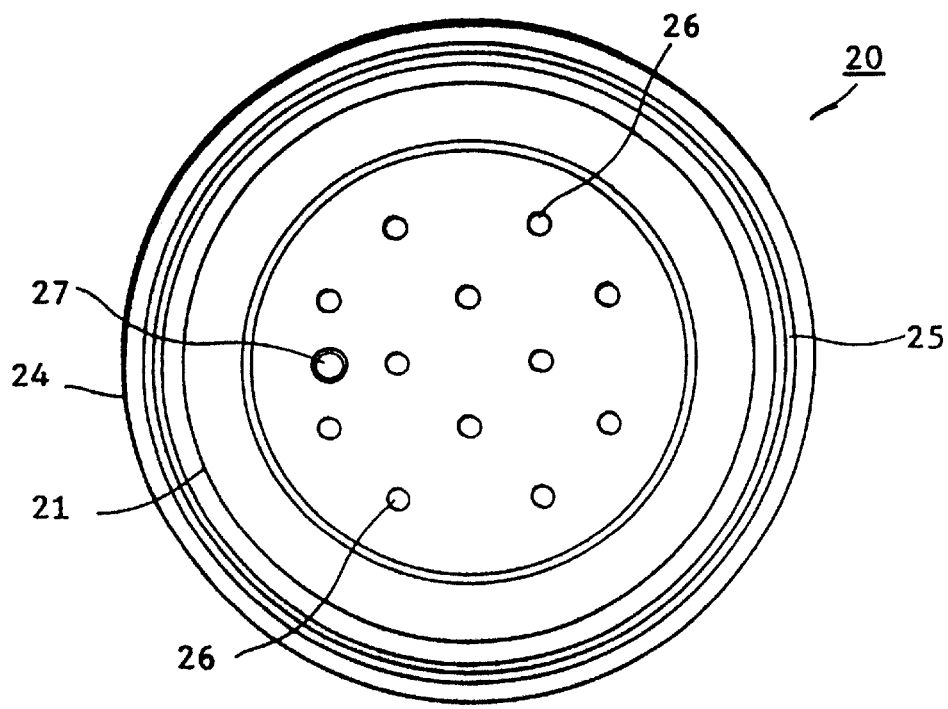
FIG. 3 is a bottom view thereof.

A blood filter cartridge of the inventors is illustrated in FIGS. 1–3. The blood filter cartridge is, as shown in FIG. 1, composed of a holder 1 consisting of a holder body 10 and a cap 20 and blood filtering material 30 consisting of a glass fiber filter 31 and a microporous membrane 32.

The holder body 10 is made of high-impact polystyrene resin, and has a glass fiber filter chamber 11a for containing the glass fiber filter 31 and a microporous membrane chamber 11b for containing a polysulfone microporous membrane as the microporous membrane 32 above the glass fiber filter chamber 11a. A monoclonal antibody to CRP was immobilized on the polysulfone microporous membrane 32. The microporous membrane chamber 11b has a diameter greater than the glass fiber filter chamber, and the periphery of the microporous membrane 32 is nipped by the step portion 19 formed on the boundary between the glass fiber filter chamber 11a and the microporous membrane chamber 12 and the bottom of the cap 20 so as not to form a leakage without passing the blood filtering material. An inclined portion 13 which stands upward slightly obliquely is formed at the outer periphery of the step portion 19, and a flange 14 is formed outward at the upper end of the inclined portion 13.

On the outer periphery of the glass fiber filter chamber 11a, 5 V-shaped circumferential grooves 12 were formed continuously at the corresponding positions to each boundary between respective glass fiber filter sheets 31 as the cutting portions.

On the other hand, the bottom of the holder body 10 is in the form of a shallow funnel, and a step portion is formed as a glass fiber filter-placing portion 15 at the periphery of the funnel-shaped disc portion 16. A nozzle-shaped blood inlet 17 is formed downward as the supply port of liquid to be filtered at the center of the funnel-shaped disc portion 16. A suction nozzle (not illustrated) is fitted to the nozzle-shaped blood inlet 17. The glass fiber filter-placing portion 15 also functions as a spacer which separates the glass fiber filter 31 from the bottom and forms a space 18 for spreading the liquid to be filtered over the whole surface of the glass fiber filter 31.

The cap 20 has an outer wall 21 and an inner wall 22 formed concentrically and a filtrate receiver 40 for storing the filtrate. The outer wall 21 is in the form of a taper having the same inclination angle as the inclined portion 13, and the outside diameter of the outer wall 21 is the same as the inside diameter of the inclined portion 13. That is, the outer wall 21 is fitable to the inclined 13 in a sealed state. A flange 24 is formed outward at the periphery of the outer wall 21, and the flange 24 is bonded to the flange 14 of the holder body 10 by ultrasonic welding. As shown in FIG. 3, a rib 25 is formed on the underside of the flange 24 so as to concentrate the ultrasonic energy there to be bonded to each other to ensure sealing. The rib 25 disappears after bonding.

As shown in FIG. 3, twelve projections 26 are formed at the bottom of the cap 20 at almost regular intervals. The projection 26 prevent the polysulfone microporous membrane 32 from adhering to the bottom.

A chimney-shaped filtrate passage 27 is formed upward penetrating the bottom of the cap 20, and a pent roof 28 is formed horizontally at the upper end of the filtrate passage 27 so as to prevent spouting of the filtrate. The pent roof 28 has the form of a combination of two half circles, as shown in FIG. 2, and the periphery of the large half circle conforms to the periphery of the filtrate passage 27. The discharge port 29 of the filtrate is provide obliquely at the upper end of the filtrate passage 27, and has the form of a lower half ellipse. As shown in FIG. 2, screens (opposite faces) 23 are formed on both sides from the filtrate outlet 29 to the upper edge of the filtrate receiver 40 in order to prevent scattering of filtrate.

The above blood filter cartridge has a diameter of the glass fiber filter chamber 11a of 20.1 mm and a depth thereof of 5.9 mm, a thickness of the peripheral wall of the holder body of 2 mm, a width of each circumferential groove of 1.5 mm, a depth thereof of 1.5 mm and a thickness of the deepest portion thereof of 0.5 mm, a diameter of the microporous membrane chamber 11b of 21.0 mm, a diameter of the upper end of the inclined portion of 22.5 mm and a depth thereof of 2.10 mm, a diameter at the lower end of the outer periphery of the outer wall 21 of 20.98 mm and a height between the underside thereof and the flange 24 of 2.0 mm, an inside diameter of the inner wall 22 of 15.0 mm, and an inside diameter of the filtrate receiver 40 of 7.5 mm. The glass fiber filter 31 consists of six glass fiber filter sheets each having a diameter of 20.0 mm and a thickness of 0.91 mm, and the microporous membrane consists of one polysulfone microporous membrane having a diameter of 20.9 mm and a thickness of 150 μm. The filtrate outlet 29 has a longitudinal diameter of 1.3 mm and a lateral diameter of 0.2 mm. The thickness of the pent roof 28 is 1 mm, and the distance between both screens (the distance of the opposite faces 23) is 2 mm.

What is claimed is:

1. A blood filter cartridge which comprises a blood filtering material and a holder containing the blood filtration material and having a blood inlet and a filtrate outlet, wherein an antibody or an antigen is immobilized on at least a part from the blood inlet to the filtrate outlet or a filtrate receiver connected to the filtrate outlet through a wall, wherein the holder has a circumferential groove for cutting off having a thickness of 0.1 to 0.5 mm at its deepest portion.

* * * * *